United States Patent
Botto et al.

(10) Patent No.: US 9,974,728 B2
(45) Date of Patent: May 22, 2018

(54) COSMETIC COMPOSITION COMPRISING A SYNERGISTIC TRF2 PROTEIN ACTIVATION SYSTEM CONSISTING OF A COMBINATION OF A PEPTIDIC SOYBEAN AND YEAST EXTRACT AND THE USES THEREOF

(71) Applicant: ISP Investments Inc., Wilmington, DE (US)

(72) Inventors: Jean-Marie Botto, Valbonne (FR); Nouha Domloge, Valbonne (FR); Frederique Portolan, Valbonne (FR)

(73) Assignee: ISP INVESTMENTS LLC, Wilmington, DE (US)

( * ) Notice: Subject to any disclaimer, the term of this patent is extended or adjusted under 35 U.S.C. 154(b) by 147 days.

(21) Appl. No.: 14/385,199

(22) PCT Filed: Mar. 8, 2013

(86) PCT No.: PCT/IB2013/000756
§ 371 (c)(1),
(2) Date: Sep. 15, 2014

(87) PCT Pub. No.: WO2013/140252
PCT Pub. Date: Sep. 26, 2013

(65) Prior Publication Data
US 2015/0064121 A1 Mar. 5, 2015

(30) Foreign Application Priority Data
Mar. 19, 2012 (FR) ...................... 12 00814

(51) Int. Cl.
| | | |
|---|---|---|
| *A61K 8/64* | (2006.01) | |
| *A61Q 19/00* | (2006.01) | |
| *A61Q 17/04* | (2006.01) | |
| *A61Q 19/08* | (2006.01) | |

(52) U.S. Cl.
CPC .............. *A61K 8/645* (2013.01); *A61K 8/64* (2013.01); *A61Q 17/04* (2013.01); *A61Q 19/00* (2013.01); *A61Q 19/004* (2013.01); *A61Q 19/08* (2013.01); *A61K 2800/522* (2013.01); *A61K 2800/5922* (2013.01)

(58) Field of Classification Search
CPC ..................................... A61K 8/645
See application file for complete search history.

(56) References Cited

U.S. PATENT DOCUMENTS

| 5,571,503 A * | 11/1996 | Mausner ............. A61K 8/345 |
| | | 424/195.16 |
| 2002/0076719 A1 | 6/2002 | Lange et al. |
| 2011/0052514 A1 | 3/2011 | Jüsten et al. |
| 2011/0129453 A1 * | 6/2011 | Harripersad ........... A61K 8/19 |
| | | 424/94.1 |
| 2013/0287715 A1 | 10/2013 | Jüsten et al. |

FOREIGN PATENT DOCUMENTS

| FR | 2826576 | 1/2003 | |
| FR | 2887772 | 1/2007 | |
| FR | 2887775 | 1/2007 | |
| FR | 2915378 | 10/2008 | |
| FR | 2915381 | 10/2008 | |
| FR | 2915384 | 10/2008 | |
| FR | 2927254 | 8/2009 | |
| FR | 2944795 | 10/2010 | |
| KR | 1020030045437 | 6/2003 | |
| WO | 98/36066 | 8/1998 | |
| WO | 2004/092395 | 10/2004 | |
| WO | WO 2011055032 A2 * | 5/2011 | ............. A61K 8/645 |
| WO | WO 2011055034 A1 * | 5/2011 | ............... A61K 8/64 |

OTHER PUBLICATIONS

EOL, Glycine Max <http://eol.org/pages/641527/overview> available Feb. 2012, accessed Nov. 5, 2015.*
Bos JD, Meinardi MM. "The 500 Dalton rule for the skin penetration of chemical compounds and drugs" Exp Dermatol. Jun. 2000;9(3):165-9.*
English translation of WO 2011055032 A2; accessed May 26, 2016.*
English translation of WO 2011055034 A1; accessed May 26, 2016.*
PCT, International Search Report, PCT/IB2013/000756, dated May 9, 2014.
Mintel, "Complete Anti-Ageing Eye Contour Care," (Dec. 2006), Database GNPD [on line] XP002689400, Database Accession No. 632286.
Mintel, Ultra All Night Repair and Moisture Cream for Face and Throat (Aug. 2010), Database GNPD [on line] XP002689401, Database Accession No. 1390859.
FR 2915384, English machine generated translation (Oct. 2008).
PCT, International Preliminary Report on Patentability (with English translation of the Written Opinion), PCT/IB2013/000756, dated Sep. 23, 2014.

* cited by examiner

*Primary Examiner* — Nicole P Babson
(74) *Attorney, Agent, or Firm* — Thompson Hine LLP

(57) ABSTRACT

A cosmetic composition having a synergistic TRF2 protein activation system consisting essentially of a combination of a peptidic soybean and yeast extract in a physiologically acceptable medium is disclosed and protecting or treating damage to the DNA of skin cells associated with aging by applying the cosmetic composition thereto, typically topically. The peptidic soybean and yeast extract is obtained by hydrolyzing at least 80% of soybeans by weight of the total weight of raw materials and at most 20% of yeast by weight of the total weight of raw materials.

13 Claims, 1 Drawing Sheet

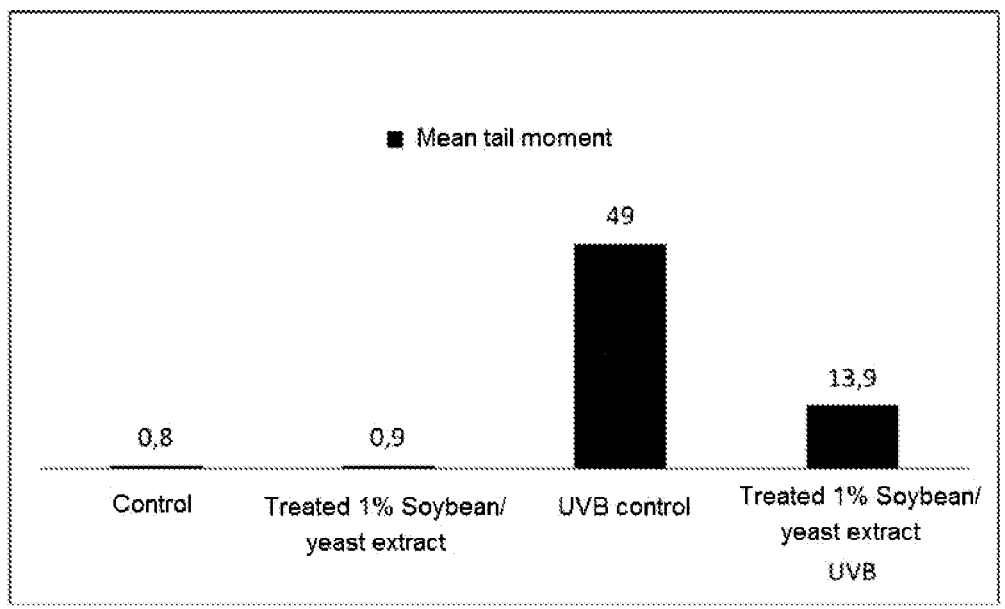

COSMETIC COMPOSITION COMPRISING A SYNERGISTIC TRF2 PROTEIN ACTIVATION SYSTEM CONSISTING OF A COMBINATION OF A PEPTIDIC SOYBEAN AND YEAST EXTRACT AND THE USES THEREOF

The present invention relates to the field of cosmetics. It relates to a cosmetic composition comprising a synergistic TRF2 protein activation system consisting of a combination of a peptidic soybean and yeast extract, more particularly intended to prevent and/or treat damage to the DNA of skin cells associated with aging and skin signs associated with aging.

Senescence is a biological process affecting all cells "normally" constituting a human being. This is conveyed in physical terms by overall aging of the human body, whether to skin cells, hair, organs, etc.

It has been scientifically demonstrated that senescence is caused particularly by telomere shortening (replicative senescence) or by acute or chronic exposure to physiological stress signals such as for example oxidative stress. One of the means explored so as to limit cells senescence and therefore human aging consists of combating telomere shortening and/or limiting the action of oxidative stress on DNA.

Telomeres are formed of repeats of the TTAGGG sequence and specific proteins. The telomeres are situated at the termini of the chromosomes and provide the stability thereof. Among the proteins binding with telomeres, the proteins TRF1 and TRF2 (TRF for telomere-binding factor) are found which bind directly with double-stranded telomeric DNA, or the protein POT1 which binds with the single-stranded 3' terminus. During cell divisions, TTAGGG units are lost in the process during replication. This loss of telomeres is partially compensated by a reverse transcriptase, telomerase, which performs de novo synthesis of telomeric repeats on termini of pre-existing telomeres, thus ensuring an optimal length.

The problem that arises is that the activity of this telomerase is extremely weak in the somatic cells, giving rise to telomeric shortening at each chromosomal replication.

One of the strategies currently used to limit skin aging and thus signs thereof consists of increasing the telomerase activity of skin cells. However, this involves a risk of immortalization of said cells, which is undesirable as immortalized cells may be linked with cancer cells.

The applicant has explored another pathway to try to delay cell senescence, by modulating the quantity of proteins associated with telomeres, and more particularly TRF2 protein. In this way, the applicant has developed a synergistic TRF2 protein activation system consisting of a combination of a peptidic soybean and yeast extract suitable for increasing the quantity of proteins associated with telomeres in skin cells.

Further TRF protein modulating compounds or telomeres stabilizers have previously been proposed as disclosed in the patent applications US20020076719, WO9836066, or WO2004092395.

Furthermore, the cosmetic use of soybean or yeast extracts has been described as having an anti-aging action on the skin (patent applications FR2915378, FR2915384, FR2915381, FR2887775, FR2887772, FR2826576) and cosmetic compositions comprising an aqueous soybean, malt and yeast extract have also been described for increasing skin elasticity (KR2003045437).

However, none of the documents cited above discloses or suggests a synergistic TRF2 protein activation system consisting of a peptidic soybean and yeast extract at defined concentrations, as disclosed in the present patent application, or the use of a cosmetic composition comprising such a TRF2 protein activation system for preventing and/or treating damage to the DNA of skin cells and skin signs associated with aging.

The TRF2 protein activation system used according to the invention particularly offers the following advantages:
- it increases the quantity of proteins associated with telomeres (TRFs) and particularly TRF2 protein in skin cells;
- it limits the increase and aggregation of vimentin cytoskeleton protein in cells having an aged cell phenotype;
- it limits the appearance of damage in skin biopsies treated with methylglyoxal;
- it limits the degradation of telomeres without modifying the quantity and/or activity of telomerase; and
- it thus prevents and/or treats damage to the DNA of skin cells and skin signs associated with aging.

The present invention firstly relates to a cosmetic composition comprising, in a physiologically acceptable medium, a synergistic TRF2 protein activation system consisting of a combination of a peptidic soybean and yeast extract obtained by hydrolyzing at least 80% of soybean by weight of the total weight of raw materials and at most 20% of yeast by weight of the total weight of raw materials.

The invention secondly relates to the cosmetic use of a composition according to the invention, for preventing and/or repairing damage to the DNA of skin cells associated with aging by increasing the quantity of TRF2 in the cells to limit the degradation of the telomeres without modifying the quantity and/or activity of telomerase.

Finally, the invention thirdly relates to cosmetic treatment methods for preventing and/or repairing damage to the DNA of skin cells associated with aging comprising the topical application of the composition according to the invention on at least a portion of the skin of the face or body.

The invention and the advantages derived therefrom will be understood more clearly on reading the description and the non-limiting embodiments hereinafter.

BRIEF DESCRIPTION OF THE DRAWINGS

FIG. 1 is a graph of the results from DNA of human fibroblasts treated with the peptidic soybean and yeast extract described herein.

The present invention thus relates to a cosmetic composition comprising, in a physiologically acceptable medium, a synergistic TRF2 protein activation system consisting of a combination of a peptidic extract obtained by hydrolyzing various selected raw materials, i.e. soybean and yeasts.

The peptidic soybean extract according to the invention is preferentially obtained from the hydrolysis of soybeans (*Glycine Max* L.) and, furthermore, the peptidic yeast extract according to the invention is preferentially obtained from the hydrolysis of biomass of yeasts of the *Saccaromyces* genus, and more particularly of the species *Saccharomyces cerevisiae*.

Preferably, the soybeans are not subjected to prior fermentation and the yeasts are freeze-dried.

In order to obtain the TRF2 protein activation system according to the invention, the peptidic soybean and yeast hydrolysates may be obtained separately and then combined to form the peptidic soybean and yeast extract according to the invention.

Preferably, the hydrolysis of the soybean and yeast takes place concomitantly, for example according to the method in example 1.

Regardless of the method used, the properties of the TRF2 protein activation system according to the invention are preserved insofar as the peptidic soybean and yeast extract is obtained by hydrolyzing at least 80% of soybean by weight of the total weight of raw materials and at most 20% of yeast by weight of the total weight of raw materials.

By way of example, the synergistic TRF2 protein activation system consists of a peptidic soybean and yeast extract obtained by hydrolyzing 85 to 92% of soybean by weight of the total weight of raw materials and 8 to 15% of yeasts by weight of the total weight of raw materials. Preferentially, the TRF2 protein activation system according to the invention is formed by hydrolyzing 90% of soybean by weight of the total weight of raw materials and 10% of yeast by weight of the total weight of raw materials.

The peptidic soybean and yeast extract forming the TRF2 protein activation system according to the invention is analyzed qualitatively and quantitatively for the physicochemical characteristics thereof and the peptidic compounds thereof; peptides, amino acids and protein fragments are assayed according to conventional techniques, well known to the one skilled in the art.

The preferred peptidic soybean and yeast extract according to the invention essentially comprises low molecular weight peptidic compounds, i.e. advantageously only contains low molecular weight peptides. Preferentially, it essentially comprises peptidic compounds having a molecular weight less than 5 kDa, i.e. advantageously the peptidic soybean and yeast extract according to the invention only comprises peptidic compounds wherein the molecular weight is less than 5 kDa.

Also, according to one advantageously embodiment of the invention, the peptidic soybean and yeast extract comprises between 16 and 18 g/L of peptidic compounds by weight of dry extract, preferentially the peptidic soybean and yeast extract according to the invention is diluted to contain between 0.5 and 5.5 g/L of peptidic compounds by weight of dry extract.

The cosmetic composition according to the invention comprising the TRF2 protein activation system and a physiologically acceptable medium is presented in a form suitable for topical application on at least a portion of the skin of the face or body.

A physiologically acceptable medium according to the invention particularly means media suitable for use in contact with human skin or skin appendages, with no risk for example of toxicity, incompatibility, instability, or allergic response.

According to one advantageous embodiment of the invention, the peptidic soybean and yeast extract forming the TRF2 protein activation system is previously solubilized in one or a plurality of physiologically acceptable solvents, conventionally used by the one skilled in the art, such as water, glycerol, ethanol, propylene glycol, butylene glycol, dipropylene glycol, diglycol ethoxylates or propoxylates, cyclic polyol, petroleum jelly, vegetable oil or a mixture of these solvents.

According to a further advantageous embodiment of the invention, the peptidic soybean and yeast extract according to the invention is solubilized in a cosmetic carrier such as liposomes, or adsorbed on organic polymer powders, mineral substrates such as talcs and bentonites, and more generally solubilized in, or bound with, any physiologically suitable carrier.

Preferably, the composition according to the invention intended to be applied topically is presented in the form of cream, oil-in-water emulsion, or water-in-oil or multiple emulsion, solution, suspension, microemulsion, aqueous or anhydrous gel, serum, or vesicular dispersion, patch, spray, unguent, ointment, lotion, colloid, milk, stick or powder.

According to one advantageous embodiment of the invention, the peptidic soybean and yeast extract is present in the cosmetic composition according to the invention at a concentration between approximately 0.0001% and 20%, and preferentially at a concentration between approximately 0.05% and 5%, more preferentially at a concentration between approximately 1% and 3% in relation to the total weight of the final composition.

More preferably, the cosmetic composition according to the invention further contains at least one further active agent. This includes but is not restricted to the following ingredient classes: further peptidic active agents, plant extracts, healing, anti-aging, anti-wrinkle, soothing, anti-radical, anti-UV agents, agents stimulating dermal macromolecule synthesis or the energy metabolism, moisturizing, antibacterial, antifungal, anti-inflammatory, anesthetic agents, agents modulating differentiation, pigmentation or depigmentation of the skin, agents stimulating nail or hair growth, etc. Preferentially, an agent having an activity in the anti-wrinkle field will be used, such as an anti-radical or antioxidant agent, or an agent stimulating dermal macromolecule synthesis, or an agent stimulating the energy metabolism. More particularly, the active agent is chosen from vitamins, phytosterols, flavonoids, DHEA and/or any of the precursors thereof or any of the chemical or biological derivatives thereof, a metalloproteinase inhibitor, or a retinoid.

Furthermore, additives such as solvents, diluents, colorants, sun filters, self-tanning agents, pigments, fillers, preservatives, odor absorbers, thickeners, emulsifiers, humectants, emollients, fragrances, antioxidants, film-forming agents, chelating agents, sequestering agents, conditioners may be added to the composition according to the invention.

In any case, one skilled in the art will ensure that these additives and the proportions thereof are chosen so as not to impede the sought advantageous properties of the composition comprising the synergistic TRF2 protein activation system consisting of a peptidic soybean and yeast extract according to the invention. These additives may be, for example, between 0.01% and 20% of the total weight of the composition. If the composition according to the invention is an emulsion, the oil phase may represent 5% to 80% by weight and preferably 5% to 50% by weight in relation to the total weight of the composition. The emulsifiers and co-emulsifiers used in the composition will be chosen from those conventionally used in the field in question. For example, they may be used in a proportion ranging from 0.3% to 30% by weight in relation to the total weight of the composition.

The cosmetic composition according to the invention, and more particularly the synergistic TRF2 protein activation system consisting of a combination of a peptidic soybean and yeast extract obtained by hydrolyzing at least 80% of soybean by weight of the total weight of raw materials and at most 20% of yeast by weight of the total weight of raw materials, increases the quantity of TRF proteins (TRF2 and/or POT1) bound with telomeres, preferentially TRF2, in the skin cells, either by increasing the protein synthesis thereof (by direct or indirect modulation of gene expression), or by further biological processes such as messenger RNA transcripts stabilization.

The TRF2 protein activation system has a synergistic action in that the combination of a peptidic soybean and yeast extract obtained by hydrolyzing at least 80% of soybean by weight of the total weight of raw materials and at most 20% of yeast by weight of the total weight of raw materials, makes it possible to increase the efficacy of the activation system by approximately 20% in respect of the increase in TRF2 expression in keratinocytes and fibroblasts in culture, compared to a 100% peptidic soybean extract for the same total quantity by weight of the total weight of raw materials.

In this way, a further object of the invention relates to the cosmetic use of the composition according to the invention for preventing and/or repairing damage to the DNA of skin cells associated with aging by increasing the quantity of TRF2 in the cells to limit telomeres degradation without modifying the quantity and/or activity of telomerase, which is important as there will thus be no risk of cell immortalization.

Damage to cell DNA in humans is repaired every day, but not entirely. Non-repaired damage thus accumulates over the years. It is thus essential to prevent and repair this damage.

Preventing damage to the DNA of skin cells denotes the protective role of the TRF2 protein activation system according to the invention on the skin cells to limit the appearance of damage to DNA.

Repairing damage to the DNA of skin cells denotes the reparative role of the TRF2 protein activation system according to the invention to previous damage to the skin cells.

Skin cells according to the invention denote cells of the epidermis and dermis, and in particular keratinocytes and fibroblasts.

Damage to the DNA of skin cells according to the invention denotes damage caused by photochemical reactions between the DNA bases, such as for example the formation of pyrimidine dimers of cyclobutane, double-strand breaks on the DNA or any other damage to the DNA following external attacks liable to be produced by the environment.

By way of example, this includes attacks such as pollution, attacks causing oxidative stress, UV radiation, particularly UVB, associated for example to overexposure to the sun, or irritant substances such as surfactants, preservatives or fragrances.

The cosmetic composition according to the invention is preferentially used in order to prevent and/or repair the occurrence of double-strand breaks on the DNA of skin cells following damage. Indeed, following damage to skin cells, particularly damage due to the UV radiation or oxidative stress, the DNA of said skin cells is liable to be subject to damage conveyed by double-strand breaks. The synergistic TRF2 protein activation system formed by the combination of a peptidic soybean and yeast extract according to the invention has demonstrated the DNA protection action thereof in respect of this type of damage.

The cosmetic composition according to the invention is also used for preventing and/or treating the skin signs of aging and the skin signs of photo-aging induced by UV radiation.

Photo-aging according to the invention denotes premature skin aging caused by prolonged and cumulative exposure to the sun.

Skin signs of aging and photo-aging according to the invention include, but are not restricted to, any visible signs on the skin caused by aging. This particularly refers to wrinkles, deep wrinkles, lines, cracks, slackening of the cutaneous and subcutaneous tissue, loss of skin elasticity and atony, loss of firmness and tone, and dermal atrophy.

The cosmetic composition according to the invention is preferentially intended to prevent and/or treat wrinkles, deep wrinkles, lines, cracks, slackening of the cutaneous and subcutaneous tissue, loss of skin elasticity and atony, loss of firmness and tone, and dermal atrophy.

Finally, a final object of the present invention relates to a cosmetic treatment method for preventing and/or repairing damage to the DNA of skin cells associated with aging comprising the topical application of the composition according to the invention on at least a portion of the skin of the face or body, wherein the composition is applied in the morning as an anti-aging day care and/or at bedtime as a repairing night care. When applied as a day care, the composition particularly protects the skin against environmental attacks, namely UV radiation, particularly UVB, by limiting the appearance of damage to the DNA of skin cells. As a night care, the composition more particularly has a reparative role in respect of any damage to the skin during the day.

In a further advantageous embodiment of the cosmetic treatment method according to the invention, the composition is applied before sun exposure, as a pre-sun care and/or after sun exposure, as an after-sun care, and thus constitutes an excellent pre-sun care particularly preventing damage to the DNA of skin cells, and/or after sun exposure, as an after-sun care more particularly so as to repair any damage to the DNA of the skin.

The following examples describe and demonstrate the efficacy of the synergistic TRF2 protein activation system according to the invention but should not be interpreted as a limitation of the present invention.

EXAMPLE 1

Method for Obtaining a Peptidic Soybean and Yeast Extract According to the Invention In order to obtain the synergistic TRF2 protein activation system according to the invention, 90% by weight of the total weight of raw materials of previously ground soybeans are mixed with 10% by weight of the total weight of raw materials of yeast biomass. The raw material mixture is placed in solution in water in a ratio by weight of 1:60, i.e. 1 kg of raw material mixture in 60 kg of water. The pH of the solution is adjusted to a value between 7 and 7.5. After adjusting the pH, 2% of bromelain and 2% of POLYCLAR® 10 (insoluble polyvinylpyrrolidone—PVPP) are added to the reaction mixture. The reaction mixture is then heated for two hours at 55° C. and inactivated for two hours at 80° C. A filtration step is used to retrieve the filtrate consisting of 20 to 25 g/L of dry matter, 19 to 22 g/L of proteins and 2 to 3 g/L of sugars.

The protein nature of this filtrate is demonstrated by polyacrylamide gel electrophoresis. For this analysis, the NuPAGE® Bis-Tris Pre-cast (Invitrogen) gels are used. The intermediate peptidic soybean and yeast extract is heated to 70° C. for 10 minutes under denaturing reducing conditions in a NuPAGE® LDS sample preparation buffer. A NuPAGE® Antioxidant solution is added in the inner vessel to prevent the reduced proteins from re-oxidizing during electrophoresis. Migration of the peptidic compounds is carried out under NuPAGE® MES migration buffer with the SeeBlue® Plus2 standard as a molecular weight marker. Staining of the peptidic compounds is performed using Coomassie Blue® R 250. The peptidic profile obtained shows a distribution of the molecular weights less than 6 kDa.

The intermediate peptidic soybean and yeast extract obtained above is then purified by means of successive filtrations using Seitz-Orion filter presses of decreasing porosity (up to 0.2 μm) to obtain a brilliant and clear solution. In this step, the soybean and yeast extract is characterized by a dry weight of 20-22 g/kg, a peptidic compound content of 18-20 g/L and a sugar content of 1-2 g/L.

This solution is then purified by removing the peptidic compounds having molecular weights greater than 5 kDa using tangential flow filtration. For this, the soybean and yeast solution is pumped under pressure via a Pellicon® holder equipped with 10 kDa Biomax Pellicon® 2 cassettes. This first filtrate is retrieved for subsequent filtration via a further 5 kDa Biomax Pellicon® 2 cassette.

At the end of purification, a brilliant and clear light yellow peptidic soybean and yeast plant extract is obtained. It is characterized by a dry weight of 18-20 g/kg, a peptidic compound content of 16-18 g/L and a sugar content between 0.3 and 0.5 g/L.

A sterilizing filtration step is then performed to obtain the peptidic soybean and yeast extract final according to the invention, diluted to 2.35 g/L of peptide compounds in 30% of glycerol.

EXAMPLE 2

Study of the Effect of the Peptidic Soybean and Yeast Extract According to Example 1 on Fibroblasts Aged by Replicative Senescence Human fibroblasts are placed in culture in a specific medium and kept in long-term culture (for more than 17 passages), using a daily application of the peptidic soybean and yeast extract according to example 1 at a concentration of 1% or 3%. A vimentin immunofluorescence detection experiment is performed on the cells at culture passages 6 and 17. The cells are then washed with PBS, fixed with 3.7% formaldehyde for 10 minutes, permeabilized using 0.2% Triton X-100 for 10 minutes (Fisher Chemical) and incubated with 1% BSA (Euromedex) for 15 minutes. An anti-vimentin antibody (Tebu Santa Cruz) is subsequently added and incubated at a 1:200 dilution for 2 hours at ambient temperature. After washing with PBS, a Donkey anti-mouse IgG antibody, conjugated with an Alexa Fluor® 488 marker are added at a 1:1000 dilution and left in incubation for one hour at ambient temperature. Finally, the sections are mounted with Fluoromount G (Electron Microscopy Science) and examined using a microscope (Nikon Eclipse 80i, magnification 40×).

Results/Conclusions:

It is observed that the aged fibroblasts treated with the peptidic soybean and yeast extract according to example 1 express less vimentin than the untreated aged fibroblasts. However, the increase in and aggregation of vimentin is associated with the cytoskeleton modifications accompanying the aging phenomenon. It can thus be concluded that the treatment with peptidic soybean and yeast extract according to the invention made it possible to limit the increase in and aggregation of vimentin due to fibroblast aging.

EXAMPLE 3

Study of the Effect of the Peptidic Soybean and Yeast Extract According to Example 1 on a Model of Biopsies Rendered Senescent In Vitro Using Methylglyoxal Human skin biopsies are rendered artificially senescent in vitro, by means of a treatment using methylglyoxal (MGO).

For this, 6 mm punches of human skin biopsies are incubated at the air-liquid interface in a specific culture medium. They are then treated with 5 mM or 10 mM of MGO (Sigma) deposited on the surface of the biopsies and in the culture medium. The biopsies are subsequently treated with either:
condition 1: 20 μL of 1×PBS, or
condition 2: 20 μL of the peptidic soybean and yeast extract according to example 1 at 1%, or
condition 3: 20 μL of the peptidic soybean and yeast extract according to example 1 at 3%.

The biopsies are fixed and included in paraffin, and are then cut into 4 μm sections using a microtome. Hematoxylin/eosin (H&E) immunolabeling is performed on the previously cut sections and the morphology and structure thereof are studied by observing with a microscope (using a Nikon Eclipse E600 microscope, 40× lens).

Results/Conclusions:

Under control condition 1, i.e. without adding peptidic extract according to the invention, it is observed that MGO caused significant damage to the skin biopsies, more specifically on the structure thereof. The damage caused is dose-dependent since more damage is observed with the quantity of 10 mM of MGO.

When the biopsies are treated with the peptidic soybean and yeast extract according to example 1, it is observed that the damage to the structures of said biopsies is much less significant than under the control conditions. It is observed that the protective effect of the peptidic soybean and yeast extract according to example 1 is dose-dependent since even less damage is observed with the 3% dose than with the 1% dose.

It can thus be concluded that the peptidic soybean and yeast extract according to the invention had a protective effect on the cell structures when said structures are subjected to stress giving rise to significant damage and early senescence.

EXAMPLE 4

Study of the Expression of TRF2 Protein by siRNA in Human Fibroblasts Treated with the Peptidic Soybean and Yeast Extract According to Example 1

In order to quantify the efficacy of the peptidic extract according to the invention, on TRF2 overexpression in a human fibroblast population, the gene coding for TRF2 was "extinguished" using siRNA (silencer RNA).

Protocol:

Fibroblast cells are placed in culture in a 6-well plate until 60% confluence. The culture medium is renewed with the addition of the peptidic soybean and yeast extract according to example 1 at 1% under the conditions described below. Then, 100 μL of a previously produced mixture containing TRF2 siRNA having a final content of 10 nM and the transfection agent are added carefully drop by drop, well by well. The cell culture plate is incubated at 37° C. and at 5% in $CO_2$ for 72 hours. The culture medium is renewed every 2 days. Four conditions were set up:
condition 1: control free from siRNA and free from active agent
condition 2: cells transfected with siRNA, free from active agent
condition 3: non-transfected cells, but treated with the active agent
condition 4: cells transfected with siRNA and treated with the active agent The TRF2 expression quantification is observed using the conventional immunotransfer technique (Western Blot) performed using an anti-TRF2 antibody and according to a conventional protocol. In order to analyze the compensation provided by the peptide in fibroblasts transfected with siRNA, the comparison will be performed in relation to untreated fibroblasts wherein the gene has not been extinguished by siRNA.

Results/Conclusions:

Between conditions 1 and 3, it is observed that the addition of the peptidic soybean and yeast extract according to example 1 gave rise to an increase in TRF2 protein expression of 17% compared to the control. Between conditions 1 and 2, the effect of siRNA on TRF2 protein expression is effectively observed: indeed, this expression is down 26%. However, adding the active agent to the cells transfected with siRNA restores TRF2 expression, and the decrease due to the presence of siRNA is only 18% compared to the control condition.

In conclusion, the peptidic soybean and yeast extract according to the invention made it possible to compensate for the decrease in TRF2 protein expression (decrease induced by the specific siRNA) in the treated fibroblasts.

EXAMPLE 5

Study of the Expression of TRF2 Protein Using siRNA in Human Keratinocytes Treated with the Peptidic Soybean and Yeast Extract According to Example 1

In order to quantify the efficacy of the peptidic extract according to the invention, on the modulation of the TRF2 expression level in a keratinocyte population, the gene coding for TRF2 was "extinguished" using siRNA.

Protocol:

Human keratinocytes in culture are optionally treated with specific TRF2 siRNA (custom siRNA, Qiagen) at a final concentration of 25 nM using the Lipofectamine™ RNAiMAX transfection technique (Invitrogen, Ref: 13778-075) and optionally treated with the ingredient at a final concentration of 1%, for 48 hours.

Four conditions were set up:
condition 1: control free from siRNA and free from active agent
condition 2: cells transfected with siRNA, free from active agent
condition 3: non-transfected cells, but treated with the active agent
condition 4: cells transfected with siRNA and treated with the active agent The cells are then washed, fixed with 3.7% formaldehyde for 10 minutes at ambient temperature. Permeabilization of the nuclei is performed using incubation with 0.2% Triton X-100 for 10 minutes at ambient temperature. The non-specific sites are blocked with 1% BSA applied for 30 minutes. The cells are incubated in the presence of a specific monoclonal mouse antibody for TRF2 (Abcam, ref: ab13579), followed by a secondary anti-mouse antibody coupled with a fluorochrome (Invitrogen, ref: A21202). The cells are then examined with an Epifluorescence microscope (Nikon Eclipse E600 microscope).

Three images per condition are analyzed and quantified using Image-Pro Analyzer 6.3 software (MediaCybernetics, Inc.). Statistical analyses are then conducted on these data using Student's t test.

Results/Conclusions:

Between conditions 1 and 3, it is observed that the addition of the peptidic soybean and yeast extract according to example 1 gave rise to an increase in TRF2 protein expression of 34.4% compared to the control. Between conditions 1 and 2, the effect of TRF2 siRNA on TRF2 protein expression is effectively observed: indeed, this expression is down 32.5%. However, adding the active agent to the cells transfected with siRNA restores TRF2 expression, and an increase of 75.5% compared to the transfected untreated cells is observed.

In conclusion, the peptidic soybean and yeast extract according to the invention made it possible to compensate for the decrease in TRF2 protein expression (decrease induced by the specific siRNA) in the treated keratinocytes.

EXAMPLE 6

Study of the Expression of TRF2 Protein in Human Fibroblasts Treated with the Peptidic Soybean and Yeast Extract According to Example 1 and Aged by Artificial Induction of Senescence In order to quantify the efficacy of the peptidic extract according to the invention, on the modulation of the TRF2 expression level, artificial induction of senescence of a fibroblast population was performed by treating the cells with specific siRNA for the FOXO3a gene for 48 hours.

Protocol:

Human fibroblasts in culture are optionally treated with specific FOXO3a siRNA (HSS177176, Invitrogen) at a final concentration of 25 nM using the Lipofectamine™ RNAiMAX transfection technique (Invitrogen, Ref: 13778-075) and optionally treated with the peptidic soybean and yeast extract according to the example 1 at a final concentration of 1%, for 48 hours.

Four conditions were set up:
condition 1: control free from siRNA and free from active agent
condition 2: cells transfected with siRNA, free from active agent
condition 3: non-transfected cells, but treated with the active agent
condition 4: cells transfected with siRNA and treated with the active agent The cells are then washed, fixed with 3.7% formaldehyde for 10 minutes at ambient temperature. Permeabilization of the nuclei is performed using incubation with 0.2% Triton X-100 for 10 minutes at ambient temperature. The non-specific sites are blocked with 1% BSA applied for 30 minutes. The cells are incubated in the presence of a specific monoclonal mouse antibody for TRF2 (Abcam, ref: ab13579), followed by a secondary anti-mouse antibody coupled with a fluorochrome (Invitrogen, ref: A21202). The cells are then examined with an Epifluorescence microscope (Nikon Eclipse E600 microscope).

Three images per condition are analyzed and quantified using Image-Pro Analyzer 6.3 software (MediaCybernetics, Inc.). Statistical analyses are then conducted on these data using Student's t test.

Results/Conclusions:

Between conditions 1 and 3, it is observed that the addition of the peptidic soybean and yeast extract according to example 1 gave rise to an increase in TRF2 protein expression of 22% compared to the control. Between conditions 1 and 2, the effect of FOXO3a-specific siRNA on TRF2 protein expression is effectively observed: indeed, this expression is down 18.9%. However, adding the active agent to the cells transfected with siRNA restores TRF2 expression (condition 4), and an increase of 26% compared to the transfected untreated cells is observed (condition 2).

In conclusion, the peptidic soybean and yeast extract according to the invention made it possible to compensate for the decrease in TRF2 protein expression artificially induced by FOXO3a-specific siRNA.

EXAMPLE 7

Study of the Protection of the DNA of Human Fibroblasts Treated with the Peptidic Soybean and Yeast Extract According to Example 1

The comet assay is a test suitable for quantifying the damage caused to DNA on a cellular level.

Protocol:

Human fibroblasts are placed in culture and treated once a day with the peptidic extract according to example 1, at a 1% concentration, between passage 3 and passage 16. They are then irradiated with UVB radiation at a rate of 50 mJ/cm$^2$, then placed back in culture in the fibroblast medium for 30 minutes.

A control culture is prepared with no treatment with the peptidic extract according to example 1.

The cells are then detached from the substrate thereof by treating with trypsin, in order to concentrate and enumerate same.

A defined number of cells (25,000 cells) is then included in a 0.75% Low Melting agarose gel, then deposited on a glass slide previously coated with 1% agarose. The slides are then immersed in a lysis solution for 1 h30 at 4° C., and then in an alkaline solution for 20 minutes at 4° C. The cells are thus lyzed and the DNA denatured. The slides are dipped in an electrophoresis solution before applying an electric field (20 V-250 mA). The DNA denatured in this way undergoes migration in the agarose gel at 4° C. Applying a fluorescent DNA dye (2 µg/ml propidium iodide) makes it possible to observe the DNA with a microscope. Damaged DNA, i.e. fragmented in multiple fragments of various sizes, migrates in a diffuse manner and appears in the form of "comets".

A quantification software is used to determine the mean Tail Moment, which increases as the DNA damage increases.

Results:

When the fibroblasts are treated with the peptidic extract according to example 1 and subjected to UVB radiation, the Tail Moment is 13.9 whereas it is 49 under the irradiated and untreated condition. The Tail moment calculated thus decreases by 71.6% (statistically highly significant decrease) compared to the irradiated control condition, i.e. the DNA of the cells subject to UVB radiation was subject to substantially less damage than under the control condition, as illustrated in FIG. 1.

Conclusions:

The peptidic extract according to example 1 at 1% protected the DNA of normal human fibroblasts subjected to UVB irradiation very significantly.

EXAMPLE 8

Sun Cream Composition

| Trade names | Ingredient (INCI names) | % by mass |
|---|---|---|
| PHASE A | | |
| | Aqua (Deionized water) | q.s. |
| | Glycerin | 3.00 |
| Versene NA2 | Disodium EDTA | 0.10 |
| | Triethanolamine | 0.50 |
| UltraThix ® P100 | Acrylic acid/VP Crosspolymer | 0.70 |
| PHASE B | | |
| | Dimethicone (100cs) | 0.50 |
| Glucamate SSE20 | PEG-20 Methyl Glucose Sesquistearate | 2.50 |
| Glucamate SS | Methyl Glucose Sesquistearate | 0.50 |
| Lanette ® 16 | Cetyl Alcohol | 1.50 |
| Ceraphyl ® SLK | Isodecyl Neopentanoate | 3.00 |
| Ceraphyl ® 230 | Diisopropyl Adipate | 2.00 |
| Escalol ® 517 | Avobenzone | 3.00 |
| Escalol ® 587 | Octisalate | 5.00 |
| Escalol ® 597 | Octocrylene | 2.00 |
| Escalol ® S | Bis-Ethylhexyloxyphenol Methoxyphenyl Triazine | 3.00 |
| PHASE C | | |
| | Cyclopentasiloxane | 5.00 |
| Si-Tec ™ RE-100 | Cyclopentasiloxane, Dimethicone/ Vinyltrimethylsiloxysilicate Crosspolymer | 1.00 |
| PHASE D | | |
| | Ethanol | 5.00 |
| Optiphen ™ ND | Phenoxyethanol, Benzoic acid, Dehydroacetic acid | 1.20 |
| PHASE E | | |
| | Peptidic soybean/yeast extract according to example 1 | 1.00 |
| | Parfum (Fragrance) | q.s. |
| | Colorant | q.s. |

The invention claimed is:

1. A cosmetic composition comprising a physiologically acceptable medium, and a synergistic TRF2 protein activation system consisting essentially of a combination of a peptidic soybean and yeast extract obtained by hydrolyzing at least 80 % of soybean by weight of the total weight of raw materials and at most 20 % of yeast by weight of the total weight of raw materials and, after purification having a dry weight of about 18 to about 20 g/kg with a peptidic compound content of about 16 to about 18 g/L by weight of dry extract and a sugar content of about 0.3 to 0.5 g/L by weight of dry extract; wherein, the peptidic soybean and yeast extract is diluted to contain between 0.5 and 5.5 g/L of peptidic compounds by weight of dry extract; and
wherein the synergistic TRF2 protein activation system comprises 1% of the total weight of the cosmetic composition.

2. The composition according to claim 1, wherein the peptidic soybean and yeast extract is obtained by hydrolyzing 90 % of soybean by weight of the total weight of raw materials and 10 % of yeast by weight of the total weight of raw materials.

3. The composition according to claim 1, wherein the peptidic soybean and yeast extract is obtained by hydrolyzing soybeans of the class *Glycine Max L.* and biomass of yeasts of the *Saccharomyces* genus.

4. The composition according to claim 1, wherein the peptidic soybean and yeast extract is obtained by hydrolyzing soybean and yeasts concomitantly.

5. The composition according to claim 1, wherein the peptidic soybean and yeast extract comprises peptidic compounds consisting essentially of peptidic compounds with a molecular weight of less than 5 kDa.

6. The composition according to claim 1, wherein the composition is in a form suitable for topical application selected from the group consisting of a cream, oil-in-water emulsion, water-in-oil emulsion, multiple emulsion, solution, suspension, microemulsion, aqueous gel, anhydrous gel, serum, vesicular dispersion, patch, spray, unguent, ointment, lotion, colloid, milk, stick and powder.

7. A method for cosmetic treatment for protecting from and/or repairing damage to the DNA of skin cells associated with aging by increasing the quantity of TRF2 in the cells without modifying the quantity and/or activity of telomerase, the method comprising: providing a cosmetic composition comprising a physiologically acceptable medium, and a synergistic TRF2 protein activation system consisting essentially of a combination of a peptidic soybean and yeast extract obtained by hydrolyzing at least 80% of soybean by weight of the total weight of raw materials and at most 20% of yeast by weight of the total weight of raw materials, after purification having a dry weight of about 18 to about 20 g/kg with a peptidic compound content of about 16 to about 18 g/L by weight of dry extract and a sugar content of about 0.3 to 0.5 g/L by weight of dry extract, wherein, the peptidic soybean and yeast extract is diluted to contain between 0.5 and 5.5 g/L of peptidic compounds by weight of dry extract; wherein the synergistic TRF2 protein activation system comprises 1% of the total weight of the cosmetic composition; and topically applying the composition to a portion of the skin of the face or body to be treated.

8. The method of claim 7, wherein the composition protects from and/or repairs double-strand breaks on the DNA of skin cells.

9. The method of claim 7, wherein the composition protects from and/or treats the skin signs of aging.

10. The method of claim 7, wherein the composition protects from and/or treats the skin signs of photo-aging induced by ultraviolet (UV) radiation.

11. The method of claim 9, wherein the skin signs of aging comprise one or more of wrinkles, deep wrinkles, lines, cracks, slackening of the cutaneous and subcutaneous tissue, loss of skin elasticity and atony, loss of firmness and tone, and dermal atrophy.

12. The method of claim 7, wherein the composition is applied in the morning as an anti-aging day care and/or at bedtime as a repairing night care.

13. The method of claim 7, wherein the composition is applied before sun exposure, as a pre-sun care and/or after sun exposure, as an after-sun care.

* * * * *